United States Patent [19]

Singh et al.

[11] Patent Number: 5,622,975

[45] Date of Patent: Apr. 22, 1997

[54] METHODS FOR INHIBITING VASCULAR SMOOTH MUSCLE CELL MIGRATION

[75] Inventors: Jai P. Singh, Carmel; Todd R. Wiernicki, Indianapolis, both of Ind.

[73] Assignee: Eli Lilly and Company, Indianapolis, Ind.

[21] Appl. No.: 457,700

[22] Filed: Jun. 1, 1995

[51] Int. Cl.$^6$ .......................... A61K 31/445; A61K 31/38
[52] U.S. Cl. ..................... 514/324; 514/212; 514/422; 514/428; 514/443; 514/448; 514/319
[58] Field of Search ................................ 514/324, 212, 514/319, 422, 428, 443, 448

[56] References Cited

U.S. PATENT DOCUMENTS

| | | | |
|---|---|---|---|
| 4,133,814 | 1/1979 | Jones et al. | 260/326.55 A |
| 4,380,635 | 4/1983 | Peters | 546/202 |
| 4,418,068 | 11/1983 | Jones | 424/267 |
| 5,075,321 | 12/1991 | Schreiber | 514/317 |
| 5,393,763 | 2/1995 | Black et al. | 514/333 |
| 5,457,113 | 10/1995 | Cullinan et al. | 514/319 |
| 5,462,937 | 10/1995 | Cullann et al. | 514/212 |
| 5,492,926 | 2/1996 | Cullinan et al. | 514/422 |

FOREIGN PATENT DOCUMENTS 652003  5/1995  European Pat. Off. .

OTHER PUBLICATIONS

Draper et al., "Effects of Raloxifene (LY139481 HCl) on Biochemical Markers of Bone and Lipid Metabolism i Healthy Postmenopausal Women", Hong Kong, Fourth Int'l Symp. on Osteoporosis, Mar. 29, 1993.

Bryant et al., "Protection from Bone Loss and Lowering of Serum Cholesterol in the Absence of Uterine Stimulation in Ovariectomized Rats", Am Soc. Bone & Min. Res., Tampa, Sep. 18–22, 1993.

Bryant et al., "Raloxifene is a Tissue Specific Estrogen Agonist", Am Soc. Bone & Min. Res., Tampa, Sep. 18–22, 1993.

Frolick et al., "In Vivo and In Vitro Metabolism of Raloxifene", Am. Soc. Bone & Min. Res., Tampa, Sep. 18–22, 1993.

Glasebrook et al., "Multiple Binding Sites for the Anti–estrogen Raloxifene", Am Soc. Bone & Min. Res., Tampa, Sep. 18–22, 1993.

Hock et al., "Combination of Raloxifene and Human Parathyoid Hormone 1–34; Increased Femur Bone Mass in Young Ovariectomized (OVX) Rats", Am. Soc. Bone & Min. Res., Tampa, Sep. 18–22, 1993.

Sato et al., "DEXA Analysis of Raloxifene Effects on the Bones From Ovariectomized Rats", Am. Soc. for Bone and Min. Res., Tampa, Sep. 18–22, 1993.

Yang et al., "Raloxifene an Anti–Estrogen, Simulates the Effects of Estrogen in Inhibiting Bone Resorption Through Regulating TGFB–3 Expression in Bone;" .Am Soc. for Bone and Min. Res., Tampa, Sep. 18–22, 1993.

Black et al., "Distinct, Structure–Related Profiles of Estrogenic and Anti–Estrogenic Activity in the Tamoxifen and LY117018 Series;" The Endocrine Society, Abstract 1982.

Black et al., "Uterine Bioassay of Tamoxifen, Trioxifene, and New Estrogen Antagonist (LY117018) in Rats and Mice," Life Sciences, 26:1980, 1453–1458.

Black et al., "Differential Interaction of Antiestrogens with Cytosol Estrogen Receptors," Molecular and Cellular Endocrinology, 22:1981, 95–103.

Black et al., "Evidence for Biological Action of the Antiestrogens LY117018 and Tamoxifen by Different Mecanisms," Endocrinology 109;1981, 987–989.

Black, L.J. "Biological Actions and Binding Properites of a New Estrogen Antagosist LY117018," In: Homone Antagonists, 129–82, 1982 (M.K. Agarwal ed.) Walter de Gruyter and Co., Berlin New York.

Black et al., LY156758: A Unique Antiestrogen Displaying High Affinity for Estrogen Receptors, Negligible Estrogenic Activity and Near–Total Estrogen Antagonism in Vivo. Presented at the Fifth Annual San Antonio Breast Cancer Symposium, San Antonio, Texas, Nov. 5–6, 1982.

Black et al., The Antiestrogenic Action of LY139481: Species Uniformity Duration of Action and Kinetics of 3H–LY139481 Distribution In Vivo. Sixty–fifth Annual Meeting of the Endocrine Society, San Antonio, Texas, Jun. 8–10, 1983, abs. 93.

Black et al., Antagonism of Estrogen Action with a New benzothiophene Derived Antiestrogen, Life Sciences, 32:1983. 1031–1036.

Black et al., The Relationship of the Antiestrogenic Efficacy of LY156758 to its Pharmacokinetics and Metabolism Following Oral Administration to Adult Ovariectomized Rats, Seventh International Congress of Endocrinology, Quebec City, Canada, Jul. 1–7, 1984, abs. 323.

(List continued on next page.)

Primary Examiner—Theodore J. Criares
Attorney, Agent, or Firm—James J. Sales; David E. Boone

[57] ABSTRACT

Methods of inhibiting vascular smooth muscle cell migration comprising administering to a human or other mammal in need of treatment an effective amount of a compound having the formula

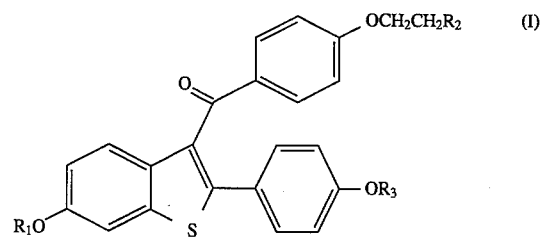

wherein $R_1$ and $R_3$ are independently hydrogen,

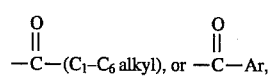

wherein Ar is optionally substituted phenyl;
$R_2$ is pyrrolidino, hexamethyleneimino, or piperidino; and pharmaceutically acceptable salts and solvates thereof.

4 Claims, No Drawings

OTHER PUBLICATIONS

Black et al., Synthesis and Antiestrogenic Activity of [3,4–Dihydro–2(4–methoxyphenyl)–1–napthalenyl] [4–[2–pyrrolidinyl) ethoxy]–phenyl] methanone, methanesulfonic acid salt, Journal of Medicinal Chemistry 22;1979, 962–966.

Black et al., Antiestrogens 2. Structure Activity Studies in a Series of 3–Aroyl–2–arylbenzo[b]thiophene Derivatives Leading to [6–Hydroxy–2–(4–hydroxyphenyl)benzo[b]thien–3–yl][4–[2–(1–piperidinyl)ethoxy]–phenyl]methanone Hydrochloride (LY156758), a Remarkably Effective Estrogen Antagonist with Only Minimal Intrinsic Estrogenicity, J. Med. Chem. 27(8), 1984, 1057–1066.

Bayard, F. et al., Estrogen Synthesis, Estrogen Metabolism, and Functional Estrogen Receptors in Rat Arterial Smooth Muscle Cells in Culture, Endocrinology, vol. 136, No. 4, 1994, p. 1523.

Brown, S.L. et al,m Stimulation of migration of huma aortic smooth muscle cells by vitronectin: implications for atherosclerosis, Cardiovascular Research, 28, 1994, pp. 1815–1820.

Choi, E.T. et al., Inhibition of neointimal hyperplasia by blocking $\alpha_v\beta_3$ integrin with a small peptide antagonist Gpen GRGDSPCA*, J. Vasc. Surg., 19, 1994, pp. 124–134.

Shinsuke Mii, et al., Transforming growth factor–beta inhibits human vascular smooth muscle cell growth and migration, Surgery, 114, 1993, pp. 464–470.

Kullmann, Anne et al., In Vitro Effects of Pentoxifylline on Smooth Muscle Cell Migration and Blood Monocyte Production of Chemotactic Activity for Smooth Muscle Cells: Potential Therapeutic Benefit in the Adult Respiratory Distress Syndrome, Am. J. Respir. Cell. Mol. Biol., 8, 1993, pp. 83–88.

Bendeck, M.P. et al., Smooth Muscle Cell Migration and Matrix Metallopropteinase Expression After Arterial Injury in the Rat, Circ Res., 75, 1994, pp. 539–545.

METHODS FOR INHIBITING VASCULAR SMOOTH MUSCLE CELL MIGRATION

BACKGROUND OF THE INVENTION

Cell migration plays an important role in wound healing, inflammation, adult respiratory distress syndrome, and malignant invasion (Savani et al., *J, Clin, Invest.* 95: 1158–1168, 1995; Kullmann et al.: *Am J. Respir. Cell. Mol. Biol.* 8: 83–88, 1993; Brooks et al., *Cell:* 79, 1157–1164, 1994). Migration of vascular smooth muscle cells from media to intima plays a critical role in neointima formation leading to the pathogenesis of vascular disease such as atherosclerosis, restenosis following PTCA, and vein bypass atherosclerosis (Jackson et al., *Arteriosclerosis and Thrombosis* 13: 1218–1226, 1993; Brown et al., *Cardiovascular Res.* 28: 1815–1820, 1995; Bell and Madri, *Am. J. Pathol.* 137: 7–12, 1990). Use of antibodies to growth factors stimulating smooth muscle cell migration or peptides that block integrin mediated cell migration have been found to inhibit neointima formation in animal models of vascular injury (Ferns et al., *Science* 253: 1129–1132, 1991., Choi et al., *J. Vasc. Surg.* 19: 125–135, 1994).

Vascular restenosis after percutaneous transluminal coronary angioplasty (PTCA) has been shown to be a tissue response characterized by an early and late phase. Thrombosis and/or vasospasms may contribute to the early phase occuring hours to days after PTCA. The late phase appears to be dominated by SMC migration, proliferation and vascular remodeling. In this disease, the increased SMC accumulation by migration from media to intima contributes significantly to the pathogenesis of the disease. The excessive proliferation and migration of vascular smooth muscle cells may be the primary mechanism to the reocclusion of coronary arteries following PTCA, atherectomy, laser angioplasty and arterial bypass graft surgery. See "Intimal Proliferation of Smooth Muscle Cells as an Explanation for Recurrent Coronary Artery Stenosis after Percutaneous Transluminal Coronary Angioplasty," Austin et al., *Journal of the American College of Cardiology* 8:369–375 (Aug. 1985).

Vascular restenosis remains a major long term complication following surgical intervention of blocked arteries by percutaneous transluminal coronary angioplasty (PTCA), atherectomy, laser angioplasty and arterial bypass graft surgery. In about 35% of the patients who undergo PTCA, reocclusion occurs within three to six months after the procedure. The current strategies for treating vascular restenosis include mechanical intervention by devices such as stents or pharmacologic therapies including heparin, low molecular weight heparin, coumarin, aspirin, fish oil, calcium antagonist, steroids, and prostacyclin. These strategies have failed to curb the reocclusion rate and have been ineffective for the treatment and prevention of vascular restenosis. See "Prevention of Restenosis after Percutaneous Transluminal Coronary Angioplasty: The Search for a 'Magic Bullet'," Hermans et al., *American Heart Journal* 122: 171–187 (July 1991).

In the pathogenesis of restinosis excessive cell proliferation and migration occurs as a result of growth factors produced by cellular constituents in the blood and the damaged arterial vessel wall which mediate the proliferation of smooth muscle cells in vascular restenosis.

Agents that inhibit the migration of smooth muscle cells are useful in the treatment and prevention of restenosis. The present invention provides for the use of compounds as smooth muscle cell migration inhibitors.

SUMMARY OF THE INVENTION

The invention provides a method of inhibiting vascular smooth muscle cell migration in a human or other mammal subject comprising administering to said subject a pharmaceutically effective dose of a compound of the formula

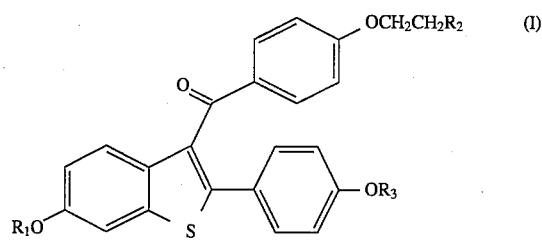

wherein $R_1$ and $R_3$ are independently hydrogen,

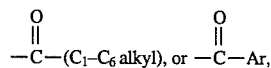

wherein Ar is optionally substituted phenyl;
$R_2$ is pyrrolidino, hexamethyleneimino, or piperidino; and pharmaceutically acceptable salts and solvates thereof.

DETAILED DESCRIPTION OF THE INVENTION

The current invention concerns the discovery that a select group of compounds, those of formula I are useful for inhibiting vascular smooth muscle cell migration. The methods of treatment provided by this invention are practiced by administering to a human or other mammal in need a dose of a compound of formula I or II, or a pharmaceutically acceptable salt or solvate thereof, that is effective to inhibit vascular smooth muscle cell migration.

The term "inhibit" is defined to include its generally accepted meaning which includes phrophylactically treating a human subject to incurring smooth muscle cell migration, and holding in check and/or treating existing smooth muscle cell migration. As such, the present method includes both medical therapeutic and/or prophylactic treatment, as appropriate.

Generally, the compound is formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

The compounds of formula I used in the methods of the current invention can be made according to established procedures, such as those detailed in U.S. Pat. Nos. 4,133, 814, 4,418,068, and 4,380,635 all of which are incorporated by reference herein. In general, the process starts with a benzo[b]thiophene having a 6-hydroxyl group and a 2-(4-hydroxyphenyl) group. The starting compound is protected, alkylated, and deprotected to form the formula I compounds. Examples of the preparation of such compounds are provided in the U.S. patents discussed above.

Included in the invention is the use of the following compounds:

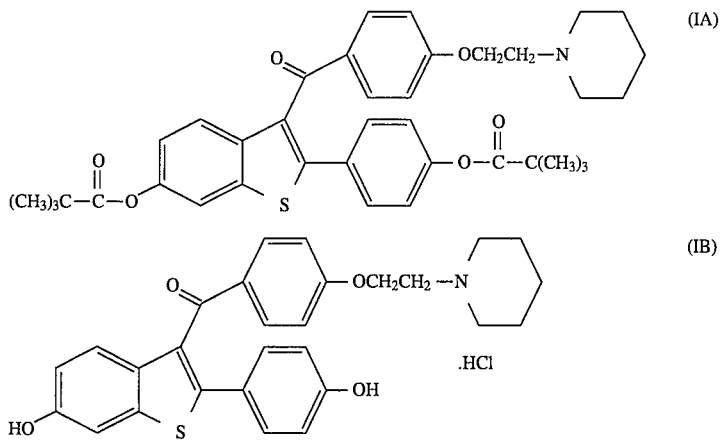

Substituted phenyl includes phenyl substituted once or twice with $C_1$–$C_6$ alkyl, $C_1$–$C_4$ alkoxy, hydroxy, nitro, chloro, fluoro, or tr(chloro or fluoro)methyl.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methane-sulfonate, naphthalene-1-sulfonate, naphthalene-2-sulfonate, p-toluenesulfonate, xylenesulfonate, tartarate, and the like. A preferable salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates and bicarbonates, as well as aliphatic and aromatic amines, aliphatic diamines and hydroxy alkylamines. Bases especially useful in the preparation of addition salts include ammonium hydroxide, potassium carbonate, sodium bicarbonate, calcium hydroxide, methylamine, diethylamine, ethylene diamine, cyclohexylamine and ethanolamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agaragar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I required to inhibit smooth muscle cell migration according to this invention will depend upon the severity of the condition, the route of administration, and related factors that will be decided by the attending physician. Generally, accepted and effective daily doses will be from about 0.1 to about 1000 mg/day, and more typically from about 50 to about 200 mg/day. Such dosages will be administered to a subject in need of treatment from once to about three times each day, or more often as needed to effectively inhibit smooth muscle cell migration.

The local delivery of inhibitory amounts of active compound for the treatment of vascular smooth muscle cell migration or restinosis can be by a variety of techniques which administer the compound at or near the affected site. Examples of local delivery techniques are not intended to be limiting but to be illustrative of the techniques available. Examples include local delivery catheters, site specific carriers, implants, direct injection, or direct applications.

Local delivery by a catheter allows the administration of a pharmaceutical agent directly to the affected lesion. Examples of local delivery using a balloon catheter are described in EPO 383 492 A2 and U.S. Pat. No. 4,636,195 (Wolinsky, Jan. 13, 1987).

Local delivery by an implant describes the surgical placement of a matrix that contains the pharmaceutical agent into the lesion. The implanted matrix releases the pharmaceutical agent by diffusion, chemical reaction, or solvent activators. Lange, *Science* 249: 1527–1533 (September, 1990).

An example of local delivery by an implant is the use of a stent. Stents are designed to mechanically prevent the collapse and reocclusion of the coronary arteries. Incorporating a pharmaceutical agent into the stent delivers the drug directly to the affected site. Local delivery by this technique is described in Kohn, *Pharmaceutical Technology* (October, 1990).

Another example is a delivery system in which a polymer that contains the pharmaceutical agent is injected into the lesion in liquid form. The polymer then cures to form the implant in situ. This technique is described in PCT WO 90/03768 (Donn, Apr. 19, 1990).

Another example is the delivery of a pharmaceutical agent by polymeric endoluminal sealing. This technique uses a catheter to apply a polymeric implant to the interior surface of the lumen. The pharmaceutical agent incorporated into the biodegradable polymer implant is thereby released at the surgical site. It is descibed in PCT WO 90/01969 (Schindler, Aug. 23, 1989).

A final example of local delivery by an implant is by direct injection of vesicles or microparticulates into the affected site. These microparticulates may be composed of substances such as proteins, lipids, carbohydrates or synthetic polymers. These microparticulates have the pharmaceutical agent incorporated throughout the microparticle or over the microparticle as a coating. Delivery systems incorporating microparticulates are described in Lange, *Science* 249: 1527–1533 (September, 1990) and Mathiowitz, et al., *J. App. Poly. Sci.*, 26:809 (1981).

Local delivery by site specific carriers describes attaching the pharmaceutical agent to a carrier which will direct the drug to the lesion. Examples of this delivery technique includes the use of carriers such as a protein ligand or a monoclonal antibody. Lange, *Science* 249: 1527–1533 (September).

Local delivery by direct application includes the use of topical applications. An example of a local delivery by direct application is applying the pharmaceutical agent directly to the arterial bypass graft during the surgical procedure.

It is usually preferred to administer a compound of formula I in the form of an acid addition salt, as is customary in the administration of pharmaceuticals bearing a basic group, such as the piperidino ring. It is also advantageous to administer such a compound by the oral route to an aging human (e.g. a post-menopausal female). For such purposes the following oral dosage forms are available.

FORMULATIONS

In the formulations which follow, "Active ingredient" means a compound of formula I.

Formulation 1: Gelatin Capsules

Hard gelatin capsules are prepared using the following:

| Ingredient | Quantity (mg/capsule) |
|---|---|
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of specific capsule formulations of the compound of formula 1 wherein the compound is raloxifene, include those shown below:

Formulation 2: Raloxifene Capsule

| Ingredient | Quantity (mg/capsule) |
|---|---|
| Raloxifene | 1 |
| Starch, NF | 112 |
| Starch flowable powder | 225.3 |
| Silicone fluid 350 centistokes | 1.7 |

Formulation 3: Raloxifene Capsule

| Ingredient | Quantity (mg/capsule) |
|---|---|
| Raloxifene | 5 |
| Starch, NF | 108 |
| Starch flowable powder | 225.3 |
| Silicone fluid 350 centistokes | 1.7 |

Formulation 4: Raloxifene Capsule

| Ingredient | Quantity (mg/capsule) |
|---|---|
| Raloxifene | 10 |
| Starch, NF | 103 |
| Starch flowable powder | 225.3 |
| Silicone fluid 350 centistokes | 1.7 |

Formulation 5: Raloxifene Capsule

| Ingredient | Quantity (mg/capsule) |
|---|---|
| Raloxifene | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

Formulation 6: Tablets

| Ingredient | Quantity (mg/tablet) |
|---|---|
| Active ingredient | 0.1–1000 |
| Cellulose, microcrystalline | 0–650 |

-continued

| Ingredient | Quantity (mg/tablet) |
| --- | --- |
| Silicon dioxide, fumed | 0–650 |
| Stearate acid | 0–15 |

The components are blended and compressed to form tablets.

Alternatively, tablets each containing 0.1–1000 mg of active ingredient are made up as follows:

Formulation 7: Tablets

| Ingredient | Quantity (mg/tablet) |
| --- | --- |
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 mL dose are made as follows:

Formulation 8: Suspensions

| Ingredient | Quantity (mg/5 ml) |
| --- | --- |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

TEST PROCEDURE

Compounds of the invention have capacity to inhibit vascular smooth cell migration, as evidenced by the following.

Porcine Aorta Smooth Muscle Cells

Porcine aorta were obtained from freshly slaughtered male castrated hogs at a local slaughterhouse. Smooth muscle cells were prepared using a procedure similar to that described previously (Bonin et al., 1989) Briefly, the aorta was cut longitudinally, and the endothelium was removed by gently scraping the lumen surface with a razor blade. The aorta was then washed several times in sterile growth medium consisting of Dubecco's Modified Eagles Medium (DMEM), 10% Fetal Bovine Serum, L-glutamine (2 mM), penicillin (100 U/ml), and streptomycin (100 ug/ml). The strips of medial smooth muscle cells were then peeled away from the adventitia and cut into 1–2 mm pieces. The explants were placed in 24 well culture dishes containing the above growth medium. Cells were observed growing from the explants within 5–7 days. After 10–14 days, the explants were removed, the cells were trypsinized, and subcultured in T75 flasks containing 15 ml of the growth medium.

Human Smooth Muscle Cells

Human coronary and aortic smooth muscle cells were purchased from Clonetics Corporation (San Diego, Calif.). Both cell types were cultured in growth medium as described for porcine smooth muscle cells.

Smooth Muscle Cells Migration Assay

Directed migration of smooth muscle cells, derived from porcine and human arteries, toward a gradient of platelet-derived growth factor was performed using a modified Boyden's chamber employing a 96 transwell system and polycarbonate filters with 8 um pores (Neuro Probe, Inc., Cabin John, N.J.). Smooth muscle cells grown in T75 flasks, were transferred to phenol red free Dubecco's Modified Eagles/F12 Medium (DMEM/F-12) containing 2% Fetal Bovine Serum, L-glutamine (2 mM), penicillin (100 U/ml), and streptomycin (100 ug/ml). After 24 hours, cells were trypsinized using phenol red free trypsin/EDTA (Gibco, BRL). The cells ($2.5 \times 10^{-6}$ cells/ml) were suspended in phenol-red free DMEM/F12 containg 1% platelet poor plasma, and various concentrations of compounds of formula I. One hundred uL of the cell suspension were added to the upper wells of the modified Boyden chamber. The wells of the lower chamber were filled with 43 ul of DMEM/F-12 containg 1% plate poor plasma, 5ng/ml PDGF and various concentration of compounds. The chambers were incubated at 37° C. in 5% $CO_2$ for 5 hours. The migration membrane was removed from the chamber and the cells from the upper side of the membrane were removed with a cotton swab. The cells migrated to the lower side of the membrane were fixed in methanol and stained with Diff-Quick staining solution (Baxter). Cell migration was quantified either spectrophotometrically using a microtiter plate reader (ThermoMax, Molecular Dynamics, Inc.) or by counting the cells in a 40× high power field (HPF) using an inverted microscope (Nikon, Inc.).

For the experiments involving preincubation of cells with the compound, drug was placed into the pretreatment medium at the indicated concentrations, in separate flasks, and incubated for 18 hours. The assay conditions of the cells in these pretreatment experiments were exactly the same as those used in the experiments described for acute drug effects.

TABLE I

Stimulation of Porcine Aortic Smooth Muscle Cell (SMC) Migration by Platelet-Derived Growth Factor (PDGF)

| PDGF (ng/ml) | SMC Migration (O.D. 650 nm) |
|---|---|
| 0.04 | 0.016 ± 0.008 |
| 0.80 | 0.009 ± 0.003 |
| 1.50 | 0.013 ± 0.007 |
| 3.00 | 0.028 ± 0.008 |
| 6.00 | 0.058 ± 0.010 |
| 12.0 | 0.052 ± 0.007 |
| 25.0 | 0.047 ± 0.009 |

TABLE II

Inhibition of PDGF Induced Porcine Aortic SMC Migration by Compound A* and β-Estradiol
SMC Migration (O.D. 650 nm)

| Concentration (nM) | Compound A | β-Estradiol |
|---|---|---|
| 0.0 | 0.053 ± 0.015 | 0.053 ± 0.015 |
| 0.1 | 0.035 ± 0.005 | 0.032 ± 0.003 |
| 1.0 | 0.030 ± 0.005 | 0.023 ± 0.003 |
| 10 | 0.032 ± 0.007 | 0.034 ± 0.006 |

*Compound A is of the Formula I, where $R_1$ and $R_3$ are hydrogen and $R_2$ is pyrrolidino.

Activity in the above indicates that the compounds of the invention are of potential in the inhibition of vascular smooth muscle cell migration and its effects.

We claim:

1. A method of treating vascular smooth muscle cell migration comprising administering to a human or other mammal in need of treatment an effective amount of a compound having the formula

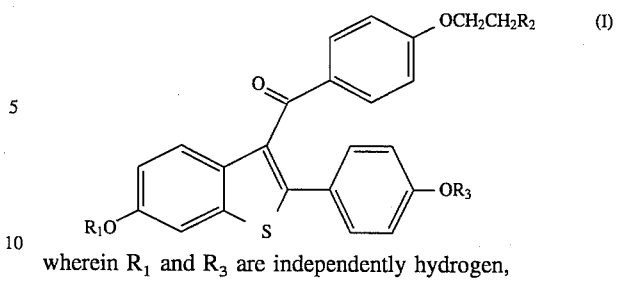

wherein $R_1$ and $R_3$ are independently hydrogen,

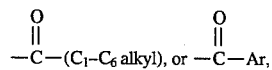

wherein Ar is optionally substituted phenyl;

$R_2$ is pyrrolidino, hexamethyleneimino, or piperidino; and pharmaceutically acceptable salts and solvates thereof.

2. The method of claim 1 wherein said compound is the hydrochloride salt thereof.

3. The method of claim 1 wherein said compound

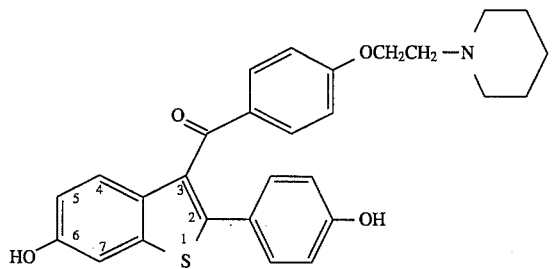

or its hydrochloride salt.

4. The method of claim 1 wherein said administration is for treatment of atherosclerosis, restenosis, inflammation, or malignant invasion.

* * * * *